United States Patent
Shan et al.

(10) Patent No.: US 10,905,379 B2
(45) Date of Patent: Feb. 2, 2021

(54) ELECTRIC BED

(71) Applicant: Keeson Technology Corporation Limited, Zhejiang (CN)

(72) Inventors: Huafeng Shan, Zhejiang (CN); Hui Cao, Zhejiang (CN); Qun Yu, Zhejiang (CN)

(73) Assignee: Keeson Technology Corporation Limited, Jiaxing (CN)

( * ) Notice: Subject to any disclaimer, the term of this patent is extended or adjusted under 35 U.S.C. 154(b) by 93 days.

(21) Appl. No.: 16/052,665

(22) Filed: Aug. 2, 2018

(65) Prior Publication Data

US 2018/0338724 A1 Nov. 29, 2018

Related U.S. Application Data

(63) Continuation of application No. PCT/CN2017/072420, filed on Jan. 24, 2017.

(30) Foreign Application Priority Data

Feb. 2, 2016 (CN) ..................... 2016 2 0103441 U

(51) Int. Cl.
  *A61B 5/00* (2006.01)
  *A61B 5/0205* (2006.01)
  (Continued)

(52) U.S. Cl.
  CPC .......... *A61B 5/6892* (2013.01); *A61B 5/0022* (2013.01); *A61B 5/02055* (2013.01);
  (Continued)

(58) Field of Classification Search
  CPC ... A61B 5/6892; A61B 5/4809; A61B 5/0022; A61B 5/02055; A61B 5/4806;
  (Continued)

(56) References Cited

U.S. PATENT DOCUMENTS 5,989,193 A * 11/1999 Sullivan ............... A61B 5/6892
  600/534
5,997,476 A * 12/1999 Brown ................. A61B 5/0002
  128/920

(Continued)

FOREIGN PATENT DOCUMENTS

| CN | 102614057 A | 8/2012 |
| CN | 104101383 A | 10/2014 |

(Continued)

OTHER PUBLICATIONS

International Search Report of PCT Patent Application No. PCT/CN2017/072420 dated Mar. 7, 2017.

(Continued)

*Primary Examiner* — Mark Bockelman

(57) ABSTRACT

An electric bed includes: a monitoring module (1), configured to monitor physical conditions of a user, and send monitoring data to a wireless communication module (2); and the wireless communication module (2), configured to send the monitoring data to a server. The server receives a setting signal sent by a terminal device, and determines whether to send an alarm signal based on the setting signal and the monitoring data. The electric bed has an intelligent help seeking function, and can comprehensively reflect a real condition of people in sleep by monitoring a plurality of vital signs, thereby reducing the probability of false alarm.

10 Claims, 2 Drawing Sheets

(51) Int. Cl.
    *A61G 7/05* (2006.01)
    *A61G 7/00* (2006.01)
    *A61B 5/11* (2006.01)
    *A61B 5/01* (2006.01)
    *A61B 5/024* (2006.01)
    *A61B 5/08* (2006.01)
(52) U.S. Cl.
    CPC ......... *A61B 5/4806* (2013.01); *A61B 5/4809* (2013.01); *A61B 5/742* (2013.01); *A61B 5/746* (2013.01); *A61G 7/00* (2013.01); *A61G 7/05* (2013.01); *A61B 5/0008* (2013.01); *A61B 5/0017* (2013.01); *A61B 5/01* (2013.01); *A61B 5/024* (2013.01); *A61B 5/0205* (2013.01); *A61B 5/0816* (2013.01); *A61B 5/0826* (2013.01); *A61B 5/1116* (2013.01); *A61B 5/6891* (2013.01); *A61G 2203/20* (2013.01)
(58) Field of Classification Search
    CPC ....... A61B 5/742; A61B 5/746; A61B 5/6891; A61B 5/0017; A61B 5/0205; A61B 5/0008; A61B 5/1116; A61B 5/01; A61B 5/024; A61B 5/0816; A61B 5/0826; A61B 5/08; A61B 5/11; A61G 7/00; A61G 7/05; A61G 2203/20; G08B 21/182; G08B 27/005
    See application file for complete search history.

(56) References Cited

U.S. PATENT DOCUMENTS

| | | | |
|---|---|---|---|
| 8,180,440 B2* | 5/2012 | McCombie | G16H 50/50 600/513 |
| 2008/0169931 A1 | 7/2008 | Gentry et al. | |
| 2012/0173319 A1* | 7/2012 | Ferrara | G06Q 30/0241 705/14.4 |
| 2014/0132413 A1 | 5/2014 | Fox et al. | |
| 2015/0216474 A1 | 8/2015 | Riley et al. | |
| 2015/0221198 A1 | 8/2015 | Collins, Jr. et al. | |
| 2015/0269827 A1 | 9/2015 | Hopkins et al. | |

FOREIGN PATENT DOCUMENTS

| | | |
|---|---|---|
| CN | 104571055 A | 4/2015 |
| CN | 204411155 U | 6/2015 |
| CN | 105125193 A | 12/2015 |
| WO | 2015101891 A1 | 7/2015 |

OTHER PUBLICATIONS

The First Examination Report of counterpart Australian Standard Patent Application No. 2017215682 dated Dec. 12, 2018.
European Search Report of counterpart European Patent Application No. 17746896.4 dated Sep. 10, 2019.

* cited by examiner

ELECTRIC BED

CROSS-REFERENCE TO RELATED APPLICATIONS

The present application is a Continuation Application of PCT patent application no. PCT/CN2017/072420 filed on Jan. 24, 2017, which claims the priority of Chinese patent application no. 201620103441.9 filed on Feb. 2, 2016. All the above are hereby incorporated by reference.

FIELD OF TECHNOLOGY

The present application relates to an electric bed, in particular to an intelligent electric bed.

BACKGROUND TECHNOLOGY

People may suddenly develop a disease during sleep, so there is a need for a system that monitors human vital sign parameters when people are asleep and is capable of alarming when an abnormality occurs.

At present, there is a care system applied to a bed, which detects a human vital sign parameter by a piezoelectric sensor, and determines whether a person who is asleep has a center of gravity movement according to a measured value of the piezoelectric sensor, and can send an alert to a preset cell phone via a wireless communication unit in an abnormal state.

However, this care system relies on only a single sensing device to measure a single human vital sign parameter, misjudgment may occur when such a single sensing device fails. In addition, the data measured by this single sensor is less reliable and cannot comprehensively reflect real vital signs of people in sleep.

SUMMARY

It is to be noted that the purpose of the present application is to overcome one or more of the disadvantages that have been found in the prior art.

For this purpose, an electric bed system controlled by an intelligent device is proposed according to the present application, which is realized by the following technical solutions:

An electric bed, including:

a monitoring module, configured to monitor physical conditions of a user and send monitoring data to a wireless communication module; and the wireless communication module, configured to send the monitoring data to a server; wherein the server receives a setting signal sent by a terminal device, and sends an alarm signal when the monitoring data are beyond thresholds set in the setting signal.

Further, a connection mean of the wireless communication module includes at least one selected from the group consisting of Wi-Fi, Bluetooth, infrared, and ZigBee.

Further, the monitoring data includes at least one selected from the group consisting of a body temperature, a heart rate, a respiratory rate, an intensity of snore, an intensity of respiration, and numbers of turning and tossing in bed.

Further, the server is a cloud server.

Further, wherein the terminal device includes a mobile phone, a tablet computer, a PDA (personal digital assistant), and a liquid crystal display screen.

Further, the terminal device displays the monitoring data.

Further, the alarm signal includes at least one information selected from the group consisting of an alarm threshold and alarm mode information.

Further, the alarm threshold includes respective thresholds of the body temperature, the heart rate, the respiratory rate, and the intensity of respiration.

Further, the alarm mode includes at least one mode selected from the group consisting of a short message, a telephone call, an e-mail, and a push message.

Further, the alarm signal is sent to a family member or a medical institution.

In the present application, comprehensive vital sign parameters, including the heart rate, the respiratory rate, the intensity of respiration, tossing, convulsion, and the like, of the user on bed may be monitored by a sensor. The vital sign parameters may be further uploaded to an internet server via the wireless communication module. Conditions in the server may be preset via the terminal device. If the server finds that the vital sign is abnormal or the user has not left the bed for a long time, the server may send an alarm to a preset personnel or a medical institution by means of the short message, the e-mail, the telephone call, or the push message. In addition, the terminal device may acquire real-time monitoring data and history data in the server for analysis of physical parameters of the user. In the present application, by monitoring a plurality of vital signs, a real condition of people in sleep can be reflected comprehensively, thereby reducing the probability of false alarm.

BRIEF DESCRIPTION OF THE DRAWINGS

It should be understood that in the present application, all features, modifications, and/or specific embodiments may be combined in various combinations, except in the cases of obvious contradictions and incompatibilities.

By reading the following non-limiting illustrative embodiments, and in conjunction with the drawings, other features and advantages of the present application will become apparent. In the figures.

DETAILED DESCRIPTION

The present application will be described in detail below with reference to the embodiments and the accompanying drawings.

Figure 1:
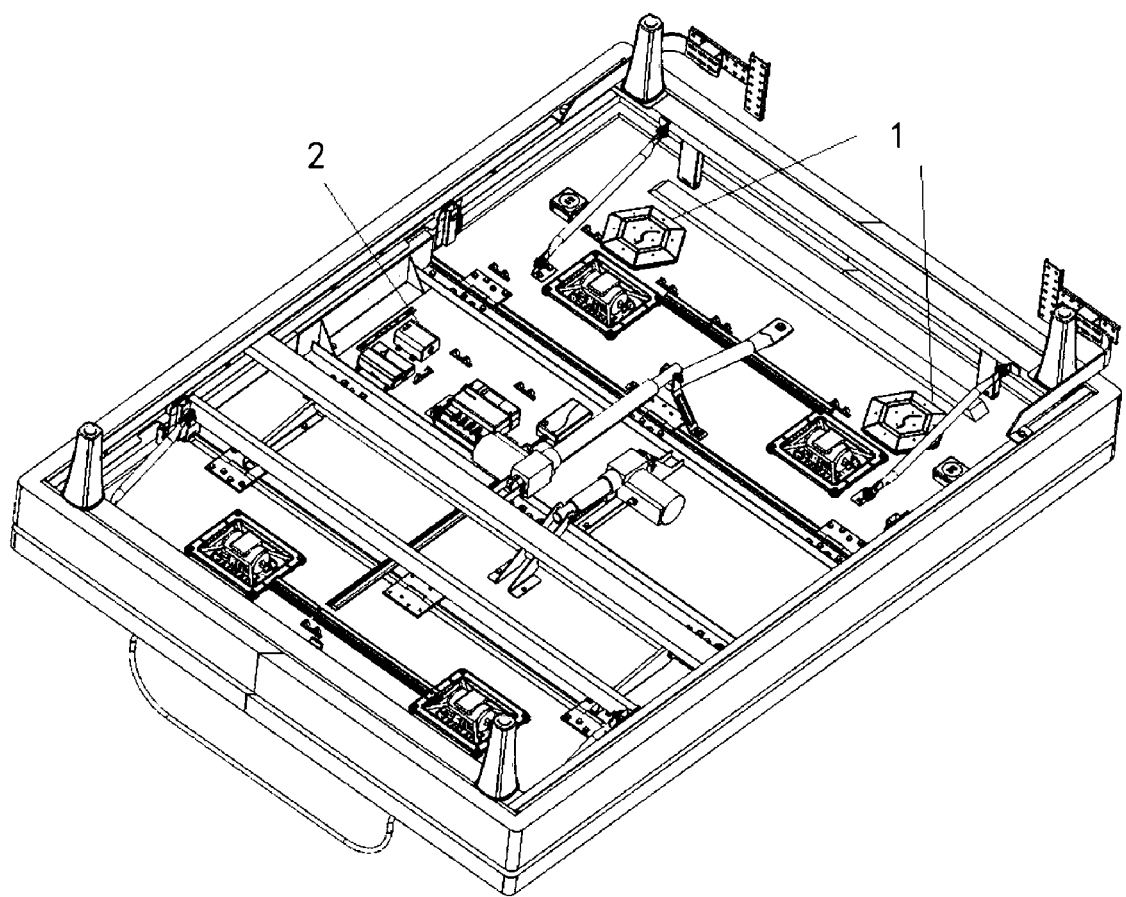
FIG. 1 is a schematic structural view showing an electric bed with an intelligent alarm function according to the present application.

With reference to FIG. 1, an electric bed with an intelligent alarm function according to the present application is shown. The electric bed provided in the present application may include a plurality of bed planks hinged to each other, a linkage mechanism connected to the plurality of bed planks, and a drive motor for driving the linkage mechanism. The electric bed may further include a monitoring module 1 and a wireless communication module 2.

The monitoring module 1 may be adapted to monitor physical conditions of a user, and may include a body temperature monitoring module, a heart rate monitoring module, a respiratory rate detector, a decibel meter, and the like. The monitoring module 1 may at least acquire monitoring data of physical conditions of the user. The monitoring data may include a body temperature, a heart rate, a respiratory rate, an intensity of snore, an intensity of respiration, numbers of turning and tossing in bed, and the like of the user. The monitoring module 1 may be adapted to send the monitoring data to the wireless communication module 2. The wireless communication module 2 may send the received monitoring data to a server. The server may store the monitoring data. Optionally, the server may send the monitoring data to a terminal device, such that the user may use the terminal device to view real-time monitoring data and history monitoring data.

The monitoring module 1 may be mounted on an upper part of a bed body of the electric bed that is close to a heart of the user so that accurate data may be acquired.

The monitoring module 1 may monitor the heart rate, the respiratory rate, the intensity of snore, the intensity of respiration, and numbers of turning and tossing in bed of the user.

The heart rate, the respiratory rate, and the intensity of respiration may be used to determine a basic physical condition of the user.

The numbers of turning and tossing in bed may be used to determine a basic sleeping condition of the user.

To avoid electromagnetic interference to the monitoring module 1 generated by wires, in one embodiment, the monitoring module 1 may communicate with the wireless communication module 2 by means of RF (Radio Frequency) wireless communication.

The wireless communication module 2 may be a Wi-Fi module, and, depending on cases, may also be a Bluetooth module, an infrared module, a ZigBee module, and the like, in order to wirelessly connect with the server. The wireless communication module 2 may be adapted to send the received monitoring data to the server.

The server may respectively and wirelessly connected to the wireless communication module 2 and the terminal device of the electric bed by means of at least one connection mean selected from the group consisting of Wi-Fi, Bluetooth, infrared, and ZigBee. The server may determine whether to generate and send an alarm signal based on a setting signal sent by the terminal device and the monitoring data.

The alarm signal may include at least one information selected from the group consisting of an alarm threshold and alarm mode information. The alarm threshold may include the respective thresholds of the body temperature, the heart rate, the respiratory rate, and the intensity of respiration. The alarm mode may include at least one mode selected from the group consisting of a short message, a telephone call, an e-mail, and a push message.

More specifically, a processing program related to the state of the electric bed may be installed in the server. On one hand, the server may receive the monitoring data of the electric bed; on the other hand, the server may receive the setting signal sent by the terminal device. The processing program may determine whether to send the alarm signal based on the monitoring data and the setting signal. For example, a threshold range of the heart rate in the terminal device may be preset from approximately 40 times/min to approximately 160 times/min, the alarm mode may be preset to short message, and terminal device may send the related setting signal to the server. When the monitoring data received by the server are beyond the range, the server may send the alarm signal by means of the short message to seek help from the outside world. On the contrary, if the monitoring data falls within the threshold range, the server will not send any alarm signal.

The server may send the alarm signal to a preset personnel or a medical institution.

The related alarm threshold set by the user via the terminal device may refer to a proposed value as follow:

the heart rate is above 160 times/min, or below 40 times/min;

the respiratory rate is above 20 times/min, or below 12 times/min; and the user has not left the bed for a long time.

Optionally, the server may store all feature parameters (such as the heart rate, the respiratory rate, the intensity of snore, the intensity of respiration, numbers of turning and tossing in bed) of the user, in order to analyze the sleeping condition of the user, thereby reducing a probability of false alarm.

Optionally, the server may receive the monitoring data indicating the physical conditions of the user of the electric bed from the wireless communication module 2, and further forward the monitoring data to the terminal device.

Optionally, the server may be a cloud (computing) server.

The terminal device may include a mobile phone, a tablet computer, a notebook computer, and the like. The terminal device may be installed with an application (App) and/or software for alerting. Using the installed application (App) and/or software, the terminal device may control a wireless module inside the terminal device to transmit the setting signal to the server. Optionally, the terminal device may communicate with the server by means of at least one connection mean selected from the group consisting of Wi-Fi, 2G, 3G, and 4G.

This type of application (App) and/or software may include a human-computer interaction interface including an option setting interface for user's selection. The user may customize various setting information of the electric bed via the interface, and further send the setting signal to the he server. The setting signal may include thresholds of various monitoring data: the heart rate, the respiratory rate, the intensity of snore, the intensity of respiration, and numbers of turning and tossing in bed of the user. The user may select the information to be set by clicking, double clicking, sliding, touching, and inputting values.

Optionally, the interaction interface may include a display interface that provides the user information data including the state of the electric bed. The state of the electric bed may include at least one selected from the group consisting of the inclination angle of each bed plank, the state of the motor, and the state of an indicator light.

Optionally, the interaction interface may further include a display interface that provides the user the monitoring data indicating the physical feature of the user. The monitoring data may include at least one selected from the group consisting of the heart rate, the respiratory rate, the intensity of snore, the intensity of respiration, and numbers of turning and tossing in bed.

The terminal device may receive the above information data and the monitoring data from the server.

Figure 2:
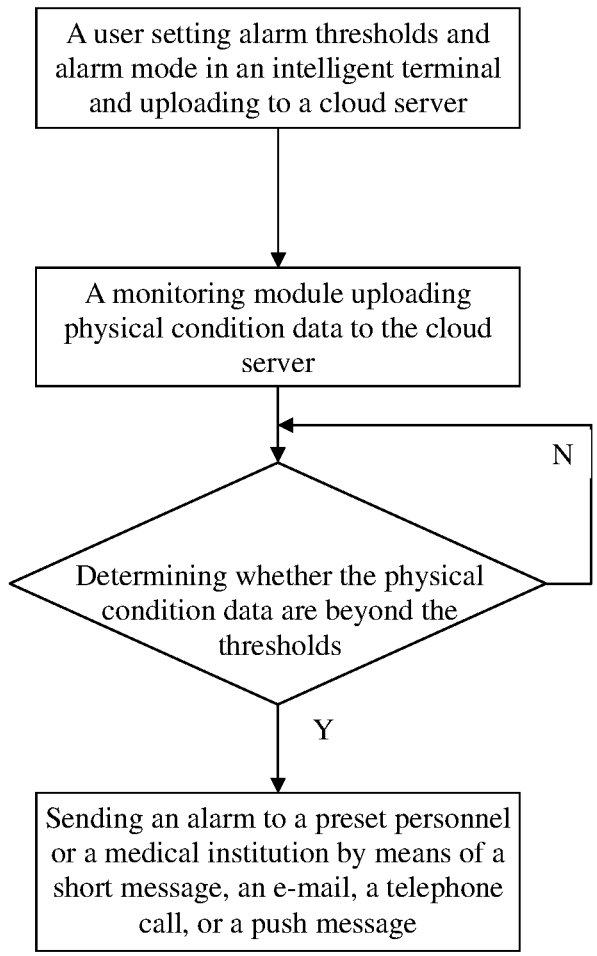
FIG. 2 is a flow chart showing operation of an electric bed with an intelligent alarm function according to the present application.

As shown in FIG. 2, a flow chart showing operation of an electric bed with the intelligent alarm function is shown.

On one hand, the monitoring module 1 of the electric bed may monitor various physical conditions of the user on the bed, and send the monitoring data indicating the physical conditions of the user to the wireless communication module 2 of the electric bed. The wireless communication module 2 may further send the monitoring data to the server.

On the other hand, the terminal device may transmit the setting signal to the server. The setting signal may include the alarm thresholds of various monitoring data and the alarm mode.

The server may determine, via the processing program, whether to generate the alarm signal based on the monitoring data and the setting signal. More specifically, when the monitoring data are beyond the set thresholds, the alarm signal will be sent; otherwise, no alarm signal will be sent. The alarm signal may be sent to a preset personnel or a medical institution by means of a short message, a telephone call, an e-mail, a push message, or the like.

Optionally, the server may send the monitoring data to the terminal device, such that the terminal device may display the monitoring data.

Optionally, the information data including the state of the electric bed may be sent to the wireless communication module 2, and the wireless communication module 2 may further send the information data to the server. The server may send the information data to the terminal device, such that the terminal device may display the information data.

The above embodiments are merely examples and do not limit the scope of the present application. Based on this, those skilled in the art can envision other embodiments that can achieve the same function within the scope of the claims of the present application.

Various embodiments and various modifications and improvements will be apparent to those skilled in the art. In particular, it should be understood that the above-described features, modifications, and/or embodiments of the present application may be combined with each other, except in the case of obvious contradictions or incompatibilities. All of these embodiments, as well as variations and modifications, are within the scope of the present application.

What is claimed is:

1. An electric bed system controlled by a terminal device, comprising:

an electric bed;

a server;

the terminal device;

a monitoring module mounted on an upper part of a bed body of the electric bed and configured to monitor physical conditions of a user in the electric bed and send monitoring data to a wireless communication module, the bed body having a front surface configured to support the user and a rear surface opposite to the front surface, and the bed body being formed in a substantially rectangular shape which has a head edge at a side of the upper part and a foot edge opposite to the head edge; the monitoring module and the wireless communication module attached to the rear surface, and the monitoring module being closer to the head edge than the wireless communication module; and the wireless communication module configured to send the monitoring data to the server;

wherein the server receives a setting signal sent by the terminal device, and sends an alarm signal when the monitoring data are beyond thresholds set in the setting signal;

wherein the monitoring data comprises a body temperature, a heart rate, a respiratory rate, an intensity of snore, an intensity of respiration, and numbers of turning and tossing in bed;

the server stores the body temperature, the heart rate, the respiratory rate, the intensity of snore, the intensity of respiration, and the numbers of turning and tossing in bed to analyze a sleeping condition of the user; and thresholds set in the setting signal are set by clicking, double clicking, sliding, touching, and inputting values of the user via an interaction interface the terminal device.

2. The system of claim 1, wherein a connection mean of the wireless communication module comprises at least one selected from the group consisting of Wi-Fi, Bluetooth, infrared, and ZigBee.

3. The system of claim 1, wherein the monitoring module comprises a pair of monitoring modules arranged on a line parallel with the head edge, the pair of monitoring modules are spaced from each other along the line.

4. The system of claim 1, wherein the server is a cloud server.

5. The system of claim 1, wherein the terminal device comprises a mobile phone, a tablet computer, or a PDA (personal digital assistant).

6. The system of claim 5, wherein the terminal device displays the monitoring data.

7. The system of claim 1, wherein the alarm signal comprises at least one information selected from the group consisting of an alarm threshold and an alarm mode information.

8. The system of claim 7, wherein the alarm threshold comprises respective thresholds of the body temperature, the heart rate, the respiratory rate, and the intensity of respiration.

9. The system of claim 7, wherein the alarm mode comprises at least one mode selected from the group consisting of a short message, a telephone call, an e-mail, and a push message.

10. The system of claim 1, wherein the alarm signal is sent to a family member or a medical institution.

* * * * *